(12) United States Patent  (10) Patent No.: US 8,718,750 B2
Lian et al.  (45) Date of Patent: May 6, 2014

(54) HEART STIMULATOR AND METHOD FOR A-V DELAY OPTIMIZATION

(75) Inventors: Jie Lian, Beaverton, OR (US); J. Christopher Moulder, Portland, OR (US); Dirk Muessig, West Linn, OR (US)

(73) Assignee: BIOTRONIK SE & Co. KG (DE)

( * ) Notice: Subject to any disclaimer, the term of this patent is extended or adjusted under 35 U.S.C. 154(b) by 16 days.

(21) Appl. No.: 13/462,134

(22) Filed: May 2, 2012

(65) Prior Publication Data

US 2012/0302904 A1  Nov. 29, 2012

Related U.S. Application Data

(60) Provisional application No. 61/490,078, filed on May 26, 2011.

(51) Int. Cl.
*A61B 5/04* (2006.01)

(52) U.S. Cl.
USPC ............................... 600/509; 607/9; 607/14

(58) Field of Classification Search
USPC ........................................ 600/509; 607/9, 14
See application file for complete search history.

(56) References Cited

U.S. PATENT DOCUMENTS

| | | | |
|---|---|---|---|
| 3,814,106 A * | 6/1974 | Berkovits | 607/9 |
| 6,682,476 B2 | 1/2004 | Alferness et al. | |
| 7,197,360 B1 | 3/2007 | Moulder et al. | |
| 7,450,995 B2 | 11/2008 | Moulder et al. | |
| 7,480,531 B1 | 1/2009 | Kroll et al. | |
| 7,532,929 B2 | 5/2009 | Mussig et al. | |
| 7,580,748 B2 | 8/2009 | Garner et al. | |
| 7,583,996 B2 | 9/2009 | Lian et al. | |
| 7,603,172 B2 | 10/2009 | Lian et al. | |
| 7,684,870 B1 | 3/2010 | Kroll et al. | |
| 7,693,575 B2 | 4/2010 | Muessig et al. | |
| 7,702,390 B1 | 4/2010 | Min | |
| 7,747,320 B1 | 6/2010 | Kroll et al. | |
| 7,761,163 B2 | 7/2010 | de Voir et al. | |
| 7,801,607 B1 | 9/2010 | Bornzin et al. | |
| 7,822,475 B2 | 10/2010 | Schomburg et al. | |
| 7,835,792 B2 | 11/2010 | Lian et al. | |
| 7,877,141 B1 | 1/2011 | Bornzin et al. | |
| 7,899,520 B2 | 3/2011 | Lian et al. | |
| 7,970,462 B2 | 6/2011 | Lefkov et al. | |
| 7,985,185 B2 | 7/2011 | De Voir et al. | |
| 8,019,406 B2 | 9/2011 | Lian et al. | |

(Continued)

OTHER PUBLICATIONS

European Search Report, Application No. 12167255.4-2305, Sep. 25, 2012.

(Continued)

*Primary Examiner* — Michael Kahelin
*Assistant Examiner* — Mallika D Fairchild
(74) *Attorney, Agent, or Firm* — Craig A. Fieschko, Esq.; DeWitt Ross & Stevens S.C.

(57) ABSTRACT

Exemplary methods and apparatuses are disclosed that provide for determination of an atrio-ventricular delay on a beat-to-beat basis by determining a P-wave duration from electric signals corresponding to electric potentials in a heart, and determining the atrio-ventricular delay on a beat-to-beat basis such that the atrio-ventricular delay for an individual heart cycle depends on the P-wave duration of a same or an immediately preceding heart cycle.

23 Claims, 4 Drawing Sheets

(56) References Cited

U.S. PATENT DOCUMENTS

| | | |
|---|---|---|
| 8,019,407 B2 | 9/2011 | Lian et al. |
| 8,024,031 B2 | 9/2011 | Nigam et al. |
| 8,060,198 B2 | 11/2011 | Lian et al. |
| 8,064,998 B2 | 11/2011 | Good et al. |
| 8,082,028 B2 | 12/2011 | Lian et al. |
| 8,090,434 B2 | 1/2012 | Lian et al. |
| 8,095,216 B1 | 1/2012 | Moulder et al. |
| 8,099,173 B2 | 1/2012 | Moulder et al. |
| 2002/0087198 A1 | 7/2002 | Kramer et al. |
| 2003/0009199 A1 | 1/2003 | Reinke et al. |
| 2003/0158586 A1 | 8/2003 | Mouchawar et al. |
| 2004/0010295 A1 | 1/2004 | Kramer et al. |
| 2005/0085862 A1 | 4/2005 | Moulder et al. |
| 2005/0165455 A1 | 7/2005 | Schomburg et al. |
| 2005/0187585 A1 | 8/2005 | Mussig et al. |
| 2007/0265539 A1 | 11/2007 | Hastings et al. |
| 2007/0265667 A1 | 11/2007 | Muessig et al. |
| 2007/0265670 A1 | 11/2007 | Lang et al. |
| 2007/0288063 A1 | 12/2007 | De Voir et al. |
| 2008/0015646 A1 | 1/2008 | Kroll et al. |
| 2008/0065161 A1 | 3/2008 | Lian et al. |
| 2008/0114409 A1 | 5/2008 | Lian et al. |
| 2008/0114411 A1 | 5/2008 | Lian et al. |
| 2008/0125822 A1 | 5/2008 | Muessig et al. |
| 2008/0125823 A1 | 5/2008 | Muessig et al. |
| 2008/0140146 A1 | 6/2008 | Garner et al. |
| 2008/0154318 A1 | 6/2008 | Albus et al. |
| 2008/0183088 A1 | 7/2008 | Lian et al. |
| 2008/0269826 A1 | 10/2008 | Lian et al. |
| 2008/0294217 A1 | 11/2008 | Lian et al. |
| 2008/0300504 A1 | 12/2008 | Lefkov et al. |
| 2009/0088814 A1 | 4/2009 | Good et al. |
| 2009/0125077 A1 | 5/2009 | Doerr et al. |
| 2009/0228061 A1 | 9/2009 | Lian et al. |
| 2009/0234411 A1 | 9/2009 | Sambelashvili et al. |
| 2009/0240157 A1 | 9/2009 | Lian et al. |
| 2009/0240298 A1 | 9/2009 | Lian et al. |
| 2009/0240300 A1 | 9/2009 | Lian et al. |
| 2009/0299203 A1 | 12/2009 | De Voir et al. |
| 2009/0312649 A1 | 12/2009 | Lian et al. |
| 2010/0049290 A1 | 2/2010 | Min et al. |
| 2010/0094370 A1 | 4/2010 | Levin et al. |
| 2010/0099995 A1 | 4/2010 | Lian et al. |
| 2010/0099996 A1 | 4/2010 | Nigam et al. |
| 2010/0100143 A1 | 4/2010 | Nigam et al. |
| 2010/0106033 A1 | 4/2010 | Lian et al. |
| 2010/0106227 A1 | 4/2010 | Min et al. |
| 2010/0217143 A1 | 8/2010 | Whittington et al. |
| 2010/0217366 A1 | 8/2010 | Moulder et al. |
| 2010/0228307 A1 | 9/2010 | Kroll et al. |
| 2010/0292596 A1 | 11/2010 | Moulder et al. |
| 2011/0087114 A1 | 4/2011 | Moulder |
| 2011/0112599 A1 | 5/2011 | Zhang et al. |
| 2011/0130669 A1 | 6/2011 | Garner et al. |
| 2011/0190841 A1 | 8/2011 | Sambelashvili et al. |
| 2011/0263987 A1 | 10/2011 | Lian et al. |
| 2012/0016249 A1 | 1/2012 | Lian et al. |

OTHER PUBLICATIONS

Ellenbogen, et al., "Primary Results from the SmartDelay Determined AV Optimization: A Comparison to Other AV Delay Methods used in Cardiac Resynchronization Therapy (SMART-AV) Trial: A Randomized Trial Comparing Empirical, Echocardiography-Guided, and Algorithmic Atrioventricular Delay Programming in Cardiac Resynchronization Therapy," Circulation 2010; vol. 122: 2660-2668.

Lian et al., "Computer modeling of ventricular rhythm during atrial fibrillation and ventricular pacing," IEEE Trans Biomed Eng., 2006(8); 53: 1512-1520.

\* cited by examiner

HEART STIMULATOR AND METHOD FOR A-V DELAY OPTIMIZATION

CROSS-REFERENCE TO RELATED APPLICATIONS

This application claims priority under 35 USC §119(e) to U.S. Provisional Patent Application 61/490,078 filed 26 May 2011, the entirety of which is incorporated by reference herein.

FIELD OF THE INVENTION

The invention refers to a heart stimulation system for stimulating at least one chamber of a heart by means of electrical stimulation pulses that are delivered when a delay time started by a cardiac event expires. The invention further refers to implantable medical devices such as implantable pacemakers and implantable cardioverter/defibrillators for atrial synchronous stimulation of a ventricle of a heart.

BACKGROUND OF THE INVENTION

Implantable heart stimulators can be used for cardiac rhythm management (CRM) for treating a variety of functional and rhythm disorders of the heart, such as bradycardia, tachycardia or fibrillation, by way of electric stimulation pulses delivered to the myocardium (i.e., the heart tissue). A sufficiently strong stimulation pulse outside a heart chamber's refractory period leads to excitation of the myocardium of that heart chamber, which in turn is followed by a contraction of the respective heart chamber.

Depending on the disorder to be treated, such heart stimulators generate electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing. The electrode lead typically carries a stimulation electrode in the region of its distal end. A stimulation pulse also is called a pace.

Similarly, pacing a heart chamber means stimulating a heart chamber by delivery of a stimulation pulse.

In order to be able to sense the contraction of a heart chamber, which occurs naturally without artificial stimulation and which is called an intrinsic contraction, the heart stimulator usually includes at least one sensing stage that is connected to a sensing electrode placed in or near the heart chamber. An intrinsic excitation of a heart chamber results in characteristic electrical potentials that can be picked up via the sensing electrode and that can be evaluated by the sensing stage in order to determine whether an intrinsic excitation—called an intrinsic event—has occurred.

Usually, a heart stimulator features separate stimulation pulse generators for each heart chamber to be stimulated. Therefore, in a dual chamber pacemaker, usually an atrial and a ventricular stimulation pulse generator for generating atrial and ventricular stimulation pulses is are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively.

Similarly, common heart stimulators feature separate sensing stages for each heart chamber of interest. In a dual chamber pacemaker usually two separate sensing stages, an atrial sensing stage and a ventricular sensing stage, are provided. The sensing stages are capable of detecting intrinsic atrial events $A_S$ (atrial sensed event) or intrinsic ventricular events $V_S$ (ventricular sensed event), respectively.

In a heart cycle, an excitation of the myocardium leads to a depolarization of the myocardium that leads to a contraction of the heart chamber. If the myocardium is fully depolarized it is unsusceptible to further excitation and is thus refractory. Thereafter, the myocardium repolarizes and thus relaxes and the heart chamber expands again. In a typical intracardiac electrogram (IEGM), depolarization of the ventricle corresponds to a signal known as the "R-wave". The repolarization of the ventricular myocardium coincides with a signal known as the "T-wave". Atrial depolarization is manifested by a signal known as the "P-wave".

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the right atrium contracts and forces the blood that has accumulated therein into the ventricle. The natural stimulus causing the right atrium to contract is conducted to the right ventricle via the atrioventricular node (AV node) with a short, natural delay referred to as the atrioventricular delay (AV-delay). Thus, a short time after the right atrial contraction (a time sufficient to allow the bulk of the blood in the right atrium to flow through the one-way valve into the right ventricle), the right ventricle contracts, forcing the blood out of the right ventricle to the pulmonary artery. A typical time interval between contraction of the right atrium and contraction of the right ventricle might is be 200 ms; a typical time interval between contraction of the right ventricle and the next contraction of the right atrium might be 800 ms. Thus, it is a right atrial contraction (A), followed a relatively short time thereafter by a right ventricle contraction (V), followed a relatively long time thereafter by the next right atrial contraction, that produces the desired AV synchrony. Where AV synchrony exists, the heart functions very efficiently as a pump in delivering life-sustaining blood to body tissue; where AV synchrony is absent, the heart functions as an inefficient pump (for example due to the loss of atrial kick when AV-delay is too short or due to diastolic regurgitation when AV-delay is too long).

Similarly, the left ventricle contracts in synchrony with the right atrium and the right ventricle with a positive or negative time delay between a right ventricular contraction and a left ventricular contraction.

A pacemaker generally shall induce a contraction of a heart chamber by delivery of a stimulation pulse (pacing pulse) to the chamber when no natural (intrinsic) contraction of the chamber occurs in due time. A contraction of a heart chamber often is called an "event".

Since a contraction may be an intrinsic contraction, which can be sensed by a sensing stage of a pacemaker, such an event is called a sensed event. A contraction due to delivery of a stimulation pulse is called a paced event. A sensed event in the atrium is called As, a paced atrial event is called Ap. Similarly, a sensed event in the ventricle is called Vs and a paced ventricular event is called Vp.

To mimic the natural behavior of a heart, a dual-chamber pacemaker provides for an AV-delay timer to provide for an adequate time delay (atrioventricular delay, AV-delay, AVD) between a natural (intrinsic) or a stimulated (paced) right atrial contraction and a right ventricular contraction. In a similar way a biventricular pacemaker provides for an adequate time delay (VV-delay, VVD) between a right ventricular contraction and a left ventricular contraction.

The time delay for a left ventricular (stimulated, paced) contraction may be timed from a scheduled right ventricular contraction which has not yet occurred, or from a natural (intrinsic) or a stimulated (paced) right atrial contraction. In the latter case a left ventricular stimulation pulse is scheduled by a time interval AVD+VVD, where VVD can be positive or negative.

To deal with possibly occurring natural (intrinsic) atrial or ventricular contractions, a demand pacemaker schedules a stimulation pulse for delivery at the end of the AV-delay or the VV-delay, respectively. The delivery of the stimulation pulse is inhibited if a natural contraction of the heart chamber to be stimulated is sensed within the respective time delay.

A natural contraction of a heart chamber can be similarly detected by evaluating electrical signals sensed by the sensing channels. In the sensed electrical signal the depolarization of an atrium muscle tissue is manifested by occurrence of a P-wave. Similarly, the depolarization of ventricular muscle tissue is manifested by the occurrence of an R-wave. The detection of a P-wave or an R-wave signifies the occurrence of intrinsic atrial, As, or ventricular, Vs, events, respectively.

A dual chamber pacemaker featuring an atrial and a ventricular sensing stage and an atrial and a ventricular stimulation pulse generator can be operated in a number of stimulation modes. For example, in VVI mode, atrial sense events are ignored and no atrial stimulation pulses are generated, but only ventricular stimulation pulses are delivered in a demand mode In AAI mode, ventricular sense events are ignored and no ventricular stimulation pulses are generated, but only atrial stimulation pulses are delivered in a demand mode. In DDD mode, both atrial and ventricular stimulation pulses are delivered in a demand mode. In such a DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

The AV-delay determines the chronological relation between an atrial event and a prescribed point of time of a ventricular event, the ventricular escape interval.

Since an optimal AV-delay may vary for different heart rates or stimulation rates and may even vary from patient to patient, the AV-delay usually is adjustable.

In order to promote natural ventricular events, often the ventricular escape interval is extended by a short time interval thus resulting in a prolonged ventricular escape interval called "AV hysteresis interval".

Ventricular pacing in one or both ventricles is required for patients with AV-block and for patients who exhibit congestive heart failure (CHF patients) that are indicated for resynchronization therapy. For patients with intact sinus rhythm or with effective atrial pacing it is beneficial to stimulate the ventricle(s) synchronous with the atrial activation, i.e., after a certain delay period after the atrial event. Standard AV-synchronous dual- or three-chamber implantable devices have a programmable AVD that can be adjusted by the physician. Several studies have shown the importance of individual AVD optimization to improve the cardiac output. Especially for CHF patients an optimization of the AVD is essential. As the pumping efficacy is impaired, the optimal timing of the ventricular stimulus in relation to the atrial event contributes significantly to the cardiac performance. If the AVD is too short, the ventricle contracts before it is completely filled by the atrial blood inflow. The active filling time is reduced. Hence the stroke volume and the cardiac output are reduced. If the AVD is too long, the ventricle contracts a while after the closure of the atrioventricular valve. Hence the passive filling time of the ventricle, i.e., the diastolic filling period during the myocardial relaxation before the atrial kick, is decreased. Also, backflow of blood from the ventricle into the atrium, e.g., mitral regurgitation, is likely. Thus also in this case the cardiac output is reduced. Similar to the heart rate also the optimal AVD depends on the activation state of the circulation. If the sympathetic tone is high, e.g., during exercise, the optimal AVD is shortened compared to the resting value.

Several methods for individual AVD optimization are state of the art. The adjustment of AVD in most cases is performed during the follow-up procedure by the physician with external measurement systems, not by the implant itself. In most of the methods the patient is in rest during the adjustment procedure and only the "static" AVD is optimized. Although modern pacing devices possess a programmable dynamic AVD, i.e., an AVD that depends on the heart rate, the dynamic values are estimated in the majority of cases.

Conventionally, the AVD optimization in clinical practice has been achieved using echocardiographic techniques, particularly by measuring the pulse-wave Doppler signals of the mitral inflow. The most representative technique is the Ritter method, which estimates the optimal AVD based on the measured interval from the QRS onset to the end of A wave (active filling). Some variants of the Ritter method have also been proposed. Alternatively, the optimal AVD can be estimated by maximizing the velocity time integral (VTI) of the aortic outflow or the mitral inflow. In addition, other Doppler-based methods for AVD optimization have also been explored, based on estimation of the cardiac output, the LV pressure derivative dP/dt, and the derived myocardial performance index (MPI), which is defined as the ratio of isovolumic contraction time plus the isovolumic relaxation time to the ejection time. Another non-invasive method for assessment of cardiac output is the thoracic impedance cardiography, which has been used for optimizing the AVD, and was found to give similar results as echocardiography. Recently, finger photoplethysmography, as a simple method for non-invasive blood pressure monitoring, has been shown to be another attractive tool for optimizing AVD in cardiac resynchronization therapy (CRT) devices.

Alternatively, the AVD can be optimized based on hemodynamic indexes that are assumed to correlate to the stroke volume or cardiac output, such as the blood pressure or its temporal derivative, the ventricular volume (e.g., through chamber impedance measurement), the blood oxygen saturation, blood pH, blood temperature, etc.

The AVD can also be optimized based on some metrics derived from the surface ECG or intracardiac electrogram (IEGM) signal. For example, an algorithm is known, which calculates the optimal AVD based on the measurement of P wave duration (PWD) from the surface ECG. The concept is that the ventricular pacing should be delivered after atrial electrical activation (end of P wave) and mechanical contraction is completed. Using an empirical formula, the sensed AVD (sAVD) is simply the sum of PWD and an add-on interval of 30 ms if the PWD is greater than or equal to 100 ms, or 60 ms if the PWD is less than 100 ms. The paced AVD (pAVD) is calculated as the sum of the sAVD and the pacing latency (e.g., 50 ms). However, both sAVD and pAVD are bounded by the measured intrinsic AV interval to ensure ventricular pacing.

Another known algorithm calculates the optimal AVD based on a patient's QRS width and intrinsic AV interval.

More specifically, the sensed AVD (sAVD) is expressed as a linear function of the QRS width and the sensed AV interval (sAVI), and the paced AVD (pAVD) is calculated as the weighted sum of the QRS width and the paced AV interval (pAVI). To ensure safety and efficacy, the calculated sAVD and pAVD are truncated to be within the range of 50 ms and 70% of the AV interval (sAVI or pAVI).

Most non-invasive methods described above share two common disadvantages. First, AVD optimization can only be performed after initial implantation or during device follow-up, when specially trained technicians are present to operate the external devices for the measurement. Second, patients are required to remain sedated or in stable supine position during the entire optimization procedure, which is time-consuming. Therefore, on the one hand, it adds to the already high cost of the device implantation. On the other hand, the AVD optimized in such a well-controlled environment do not guarantee to be optimal in ambulatory conditions.

The AVD optimization methods based on measurement of hemodynamic parameters usually require special sensors, and their technical reliability has not been proven.

The algorithm which calculates the optimal AVD based on the measurement of P wave duration (PWD) from the surface ECG assumes there is a linear relationship between optimal AVD and the PWD. The add-on value to the measured PWD is fixed without any consideration of the autonomic status of the heart or recovery period of the AV node, both of which have been known to affect the native AV conduction.

The algorithm that calculates the optimal AVD based on patient's QRS width and intrinsic AV interval assumes the optimal AVD is linearly related to QRS width and intrinsic AV interval. This assumption is not supported by clinical evidence. In fact, the recent SMART-AV Trial (Ellenbogen et al., "Primary Results From the SmartDelay Determined AV Optimization: A Comparison to Other AV Delay Methods Used in Cardiac Resynchronization Therapy (SMART-AV) Trial: A Randomized Trial Comparing Empirical, Echocardiography-Guided, and Algorithmic Atrioventricular Delay Programming in Cardiac Resynchronization Therapy," *Circulation* 2010; vol. 122: 2660-2668) showed that the optimal AVD determined using this method was not superior to a fixed AVD of 120 ms.

How to achieve optimal rate-adaptation of AVD in CRT devices remains unclear. On the one hand, changes in the AV nodal conduction of intrinsic rhythm associated with exercise may alter the degree of biventricular (BiV) capture and affect the efficacy of CRT. Thus rate-adaptive AVD in CRT seems a reasonable approach for ensuring BiV capture. On the other hand, in heart failure patients, shortening of AVD at elevated heart rate may compromise the ventricular filling and result in decreased preload, and thus may have adverse effects on LV systolic function. Dynamic adjusting of AVD has also been the focus of research for decades. Although rate-adaptive AVD (i.e., shortening device AVD at increased heart rate) has been a common feature in the dual-chamber pacemakers, there is scarce literature regarding the rate-adaptation of the AVD in CRT devices.

There is still a need for an apparatus and method for optimizing pacemaker A-V delay (AVD).

SUMMARY OF THE INVENTION

To meet this need an exemplary apparatus and method for optimizing pacemaker A-V delay (AVD) on a beat-to-beat basis by taking into account inter-atrial conduction time, AV nodal recovery time, and the autonomic status of the patient is presented.

According to one aspect, this is achieved by an exemplary implantable heart stimulator that can be connected or is connected to at least one electrode lead for picking up electric potentials corresponding to myocardial contraction. The implantable heart simulator includes an evaluation unit connected or connectable to the electrode lead and configured to evaluate electric signals corresponding to the electric potentials. The implantable heart simulator further includes a control unit that is configured to schedule a ventricular stimulation pulse at expiry of an atrio-ventricular delay (AVD) that is triggered by an atrial event. The evaluation unit is configured to determine a P-wave duration from the electric signals corresponding to the electric potentials. The control unit is configured to determine an atrio-ventricular delay on a beat-to-beat basis such that an atrio-ventricular delay for an individual heart cycle depends on the P-wave duration of a same or an immediately preceding heart cycle. The P-wave duration can also be determined as the average of multiple preceding heart cycles.

Thus, the exemplary heart stimulator is able to automatically determine the optimal AVD on beat-to-beat basis for implantable pacemakers, implantable cardioverter-defibrillators (ICDs), CRTs, and CRT/Ds by taking into account the inter-atrial conduction time (IACT). While the importance of inter-atrial conduction time (TACT) on AVD optimization has long been recognized, and studies have suggested that there may be a linear relationship between IACT and optimal AVD, the IACT measurement typically requires special sensors or echo equipment. Moreover, previous studies failed to demonstrate sufficiently high correlation coefficient of the linear regression model between IACT and the optimal AVD. Therefore, significant deviance may exist between the model predicted optimal AVD and the truly optimal AVD.

The IACT is a critical interval in the interaction between left atrium (LA) emptying and LV filling. Programming AVD that is excessively longer than IACT will frequently cause diastolic mitral regurgitation, whereas programming AVD that is shorter than IACT will frequently cause P wave reversal or increased venous and pulmonary pressure because of atrial contraction against a closed mitral valve. Exemplary versions of the invention recognize that the IACT can be approximated by the PWD, which could be measured on surface ECG or IEGM recorded from far-field sensing vectors.

The AV node has a rich autonomic innervation and is supplied by both sympathetic and parasympathetic nerve fibers. This autonomic innervation has a major role in the time required for the impulse to pass through the AV node. Conventional pacemakers support dynamic AV delay that is adaptive to the heart rate, which is mainly governed by the sympathetic input at high heart rate. The inhibition of vagal tone is released at low heart rate, and enhanced vagal tone can further slow the AV nodal conduction. Therefore, the conventional rate-adaptive AV delay feature may not account for the change in patient's vagal tone.

Another unique property of the AV node is that the AV conduction time is inversely related to the AV nodal recovery time. The AV nodal recovery time refers to the interval between the end of previous AV nodal refractory period and the following AV nodal activation time (Lian et al., "Computer modeling of ventricular rhythm during atrial fibrillation and ventricular pacing," *IEEE Trans Biomed Eng,* 2006(8); 53: 1512-1520). In a healthy heart, shortening the AV nodal recovery time leads to longer AV conduction time whereas lengthening the AV nodal recovery time results in shorter AV conduction time when the autonomic tone of the heart is stable. To our knowledge, there is no prior art that determines the optimal device AVD by taking into account the recovery-dependency property of the AV node.

Preferably the control unit is configured to calculate the atrio-ventricular delay as P-wave duration plus Δ duration, where Δ is a function of an AV nodal recovery time and an underlying autonomic status of the patient. According to a further preferred version Δ is inversely related to the AV nodal recovery time.

Preferably, the control unit is configured to calculate the atrio-ventricular delay on a beat-by-beat basis and to adjust Δ on a beat-by-beat basis.

The AV nodal recovery time can be approximated by a V-A interval determined from an intracardiac electrocardiogram derived from picked up electric potentials. The autonomic status of the heart can be assessed by means of an accelerometer sensor, a minute ventilation sensor, a close-loop-stimulation (CLS) sensor, a short-term heart rate variability (HRV) analysis, and/or intracardiac impedance measurements.

According to a further preferred version the heart stimulator is configured to deliver a cardiac resynchronization therapy and the control unit is further configured to bound the atrioventricular delay by an intrinsic atrioventricular conduction time.

According to a further aspect, an object of the invention can be achieved by an exemplary method to determine an atrio-ventricular delay on a beat-to-beat basis wherein the method includes the steps of: determining a P-wave duration from electric signals corresponding to electric potentials in a heart, and determining the atrio-ventricular delay on a beat-to-beat basis such that the atrio-ventricular delay for an individual heart cycle depends on the P-wave duration of a same or an immediately preceding heart cycle.

Preferably the atrio-ventricular delay is calculated as P-wave duration plus Δ duration, where Δ is a function of an AV nodal recovery time and an underlying autonomic status of the patient.

In a most preferred version, the inter-atrial conduction time is determined based on P wave duration (PWD) measurement in surface ECG or intracardiac electrogram (IEGM). The optimal AVD is calculated as PWD plus Δ duration, where Δ is a function of the AV nodal recovery time and the underlying autonomic status of the patient. In contrast to the above mentioned solutions, Δ may be adjusted on a beat-by-beat basis.

The AV nodal recovery time can be approximated by the R-P interval in the surface ECG or the V-A interval in the IEGM. The autonomic status of the heart can be assessed by different means, including but not limited to, accelerometer sensors, minute ventilation sensors, close-loop-stimulation (CLS) sensors, short-term heart rate variability (HRV) analysis, intracardiac impedance measurements, etc. For CRT or CRT-D devices, the optimal AVD is further bounded by the intrinsic AV conduction time.

The exemplary apparatuses and methods disclosed herein thus provide for determining optimal AVD on a beat-by-beat basis by taking into account inter-atrial conduction time, AV nodal recovery time, and/or autonomic status of the patient.

BRIEF DESCRIPTION OF THE DRAWINGS

The foregoing and other objectives, advantages and novel features of the present invention can be understood and appreciated by referencing to the following detailed description of exemplary versions of the invention, taken in conjunction the accompanying drawings, in which.

DETAILED DESCRIPTION OF EXEMPLARY VERSIONS OF THE INVENTION

Figure 1:
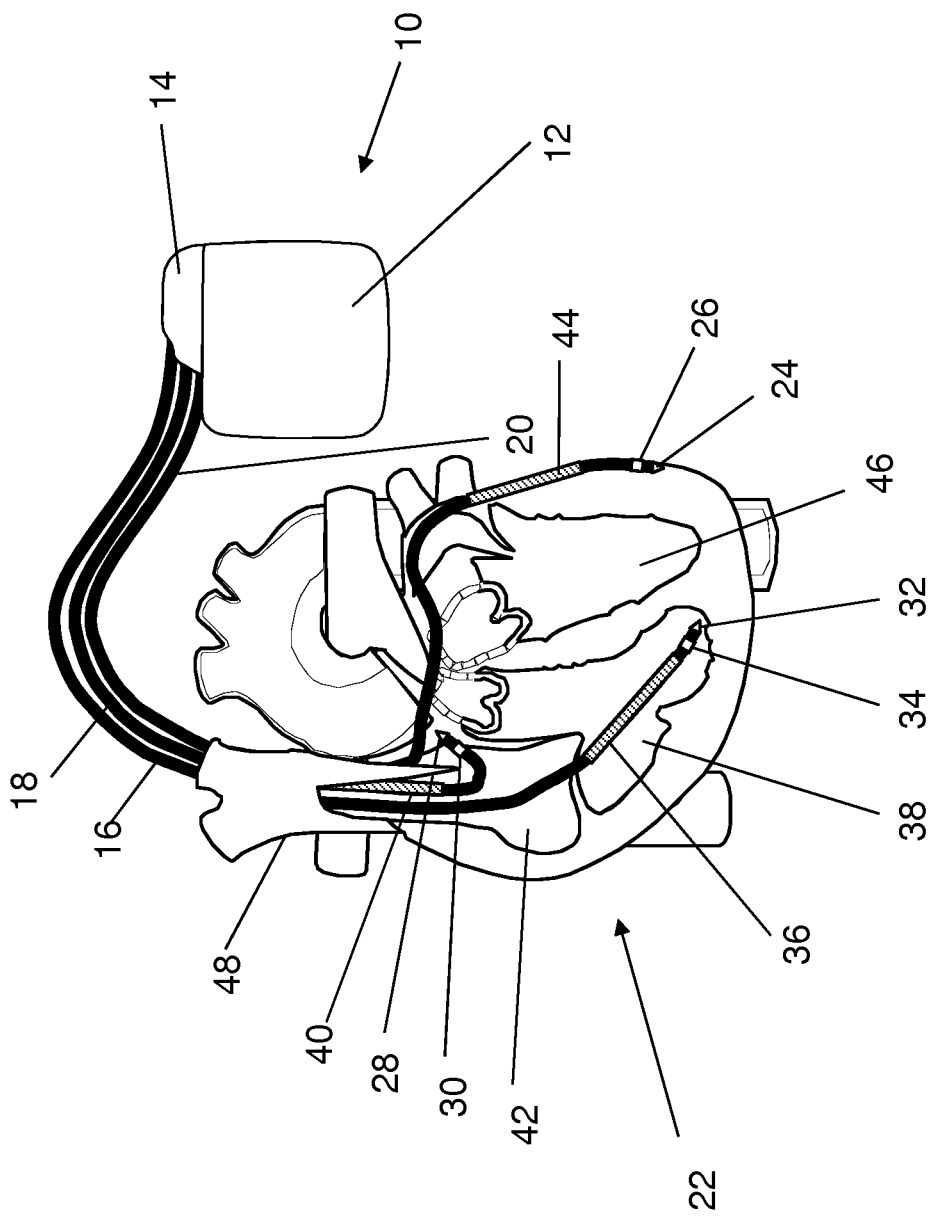
FIG. 1 illustrates an exemplary heart stimulator connected to electrode leads that are placed in a heart together with an external device.

In FIG. 1, an exemplary implantable heart stimulator 10 is depicted that includes a case 12 and header 14.

The heart stimulator 10 is connected to three electrode leads, namely a right ventricular electrode lead 16, a right atrial electrode lead 18 and a left ventricular electrode lead 20.

The left ventricular electrode lead 20 is designed to pass through the coronary sinus of heart 22. Left ventricular electrode lead 20 includes a left ventricular tip electrode 24 at the distal end, a left ventricular electrode lead 20 and a left ventricular ring electrode 26.

Atrial electrode lead 18 includes a right atrial tip electrode 28 at the distal end of right atrial electrode lead 18 and a right atrial ring electrode 30.

The right ventricular electrode lead 16 includes right ventricular tip electrode 32 at the distal end of right ventricular electrode lead 16 and a right ventricular ring electrode 34.

In order to illustrate that heart stimulator 10 may be adapted to act as an implantable car-dioverter/defibrillator (ICD), ventricular electrode lead 16 also exhibits a ventricular shock coil 36 for the delivery of defibrillation shocks to right ventricle 38 of heart 22. Likewise, atrial electrode lead 18 includes a superior vena cava (SVC) shock coil 40 for the delivery of defibrillation shocks to a right atrium 42 of heart 22 and left ventricular electrode lead 20 includes a left ventricular shock coil 44 for the delivery of defibrillation shocks to a left ventricle 46.

Each electrode and shock coil of electrode leads 16, 18 and 20 is separately connected to an electric circuit enclosed by case 12 of heart stimulator 10 by way of electrical contacts of a plug (not shown) at the proximal end of each electrode lead 16, 18 and 20 and corresponding contacts (not shown) in header 14 of heart stimulator 10.

Figure 2:
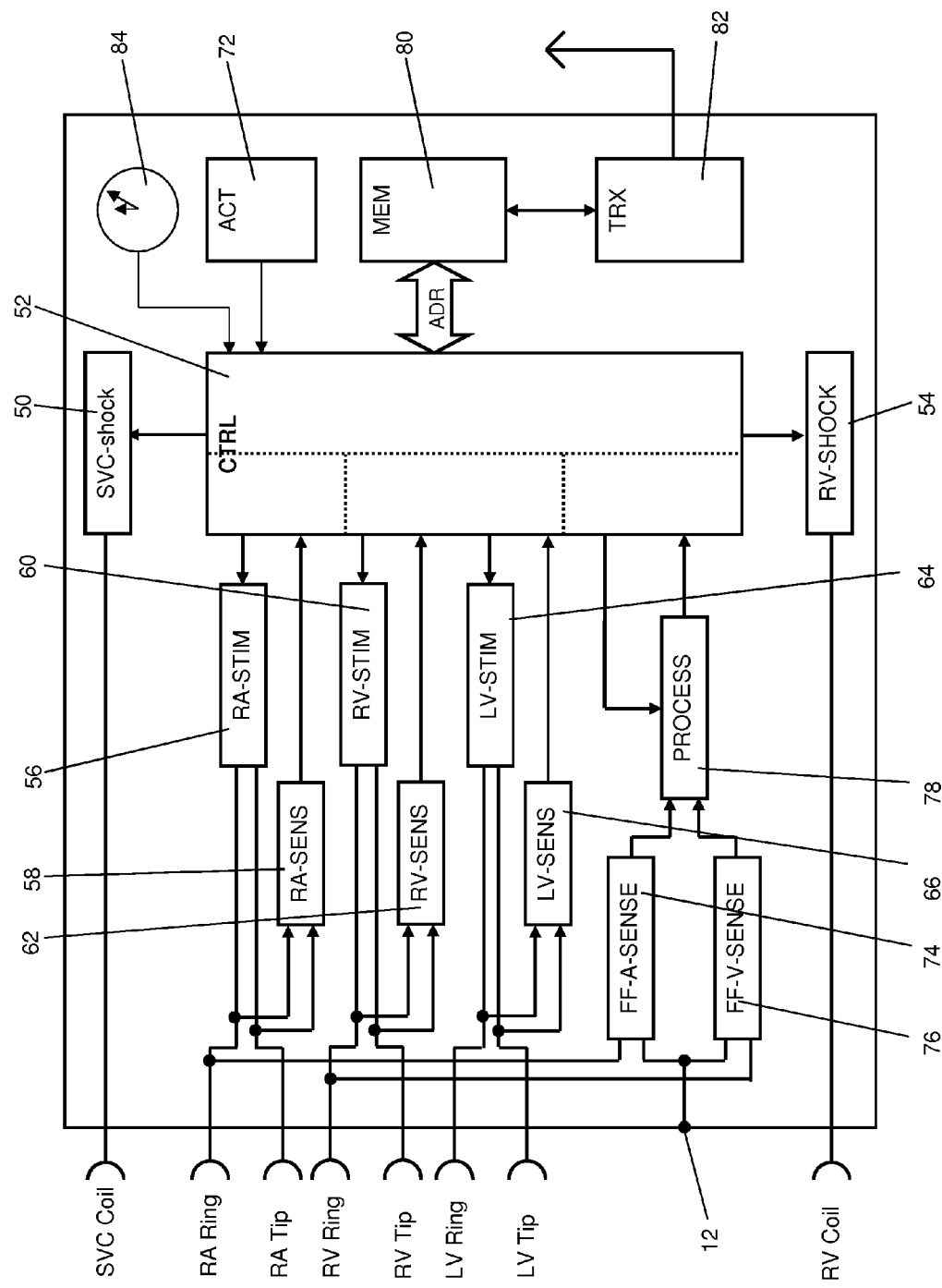
FIG. 2 shows a schematic block diagram of the heart stimulator of FIG. 1.

Referring to FIG. 2, SVC shock coil (SVC Coil) 40 is connected to right atrial shock generator SVC-shock 50 that is controlled by a control unit CTRL 52 of heart stimulator 10.

Similarly, right ventricular shock coil (RV Coil) 36 is connected to a right ventricular shock generator RV-shock 54 that is also connected to control unit CTRL 52.

Right atrial tip electrode RA Tip 28 and right atrial ring electrode RA Ring 30 are both connected to a right atrial stimulation pulse generator RA-STIM 56 and a right atrial sensing stage RA-SENS 58 that are internally both connected to control unit CTRL 52.

Right atrial stimulation pulse generator RA-STIM 56 is adapted to generate atrial stimulation pulses of sufficient strength to cause an excitation of atrial myocardium by an electrical pulse delivered via right atrial tip electrode RA Tip 28 and right atrial ring electrode RA Ring 30. Preferably, means are provided to adapt the right atrial stimulation pulse strength to the stimulation threshold in the right atrium.

Right atrial sensing stage RA-SENS 58 is adapted to pick up myocardial potentials indicating an intrinsic atrial excitation that corresponds to a natural atrial contraction. By way of right atrial sensing stage RA-SENS 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage RA-SENS 58 prior to expiration of an atrial escape interval.

In a similar manner, right ventricular ring electrode RV Ring 34 and right ventricular tip electrode RV Tip 32 are connected to right ventricular stimulation pulse generator RV-STIM 60 and to a right ventricular sensing stage RV-SENS 62 that in turn are connected to control unit CTRL 52. By way of right ventricular tip electrode RV Tip 32, right ventricular ring electrode RV Ring 34, right ventricular stimulation generator RV-STIM 60 and right ventricular sensing stage RV-SENS 62, right ventricular stimulation pulses can be delivered in a demand mode to the right ventricle 38 of heart 22.

In the same way, left ventricular tip electrode LV Tip 32 and left ventricular ring electrode LV Ring 26 are connected to the left ventricular stimulation pulse generator LV-STIM 64 and the left ventricular sensing stage LV-SENS 66 that are internally connected to control unit CTRL 52 and that allow for stimulating a left ventricle 70 of heart 22.

Triggering and inhibition of delivery of stimulation pulses to the right atrium, the right ventricle or the left ventricle is controlled by control unit CTRL 52, in a manner known to a person skilled in the art. The timing that schedules delivery of stimulation pulses if needed is controlled by a number of intervals that at least partly may depend on a hemodynamic demand of a patient. The hemodynamic demand is sensed by means of an activity sensor ACT 72 that is connected to control unit CTRL 52. Activity sensor ACT 72 allows for rate adaptive pacing, wherein a pacing rate depends on a physiological demand of a patient that is sensed by a way of activity sensor ACT 72.

For the purpose of composition of a far-field intra-atrial electrogram (AEGM) and a far-field intra-ventricular electrogram (VEGM), a far-field atrial sensing stage FF-A-SENSE 74 and a far-field ventricular sensing stage FF-V-SENSE 76, respectively, are provided. The far-field atrial sensing stage FF-A-SENSE 74 is connected to a case electrode that is formed by at least an electrically conducting part of case 12 of the heart stimulator 10 and to the right atrial ring electrode RA Ring 30. Alternatively, far-field atrial sensing stage FF-A-SENSE 74 could be connected to the right atrial tip electrode RA Tip 28 or to the SVC coil electrode SVC Coil 40. A switch for switching between these electrodes could be provided.

The far-field ventricular sensing stage FF-V-SENSE 76 is also connected to the case electrode formed by a case 12 of heart stimulator 10 and to the right ventricular ring electrode RV Ring 34. Alternatively, far-field ventricular sensing stage FF-V-SENSE 76 can be connected to right ventricular tip electrode RV Tip 32 or right ventricular coil electrode RV coil 36. A switch for switching between these electrodes could be provided.

Both far-field atrial sensing stage FF-A-SENSE 74 and far-field ventricular sensing stage FF-V-SENSE 76 are adapted to picking up far-field intra-cardiac electrograms and to generating electrogram signals that are fed to a processing unit PROCESS 78. Processing unit 78 is adapted to filter and scale each electrogram signal received from either the far-field atrial sensing stage FF-A-SENSE 74 or the far-field ventricular sensing stage FF-V-SENSE 76, or both independently from each other, and to sum the resulting filtered and scaled electrogram signals in order to generate the composite pseudo far-field electrogram signal (pseudo ECG).

Figure 3:
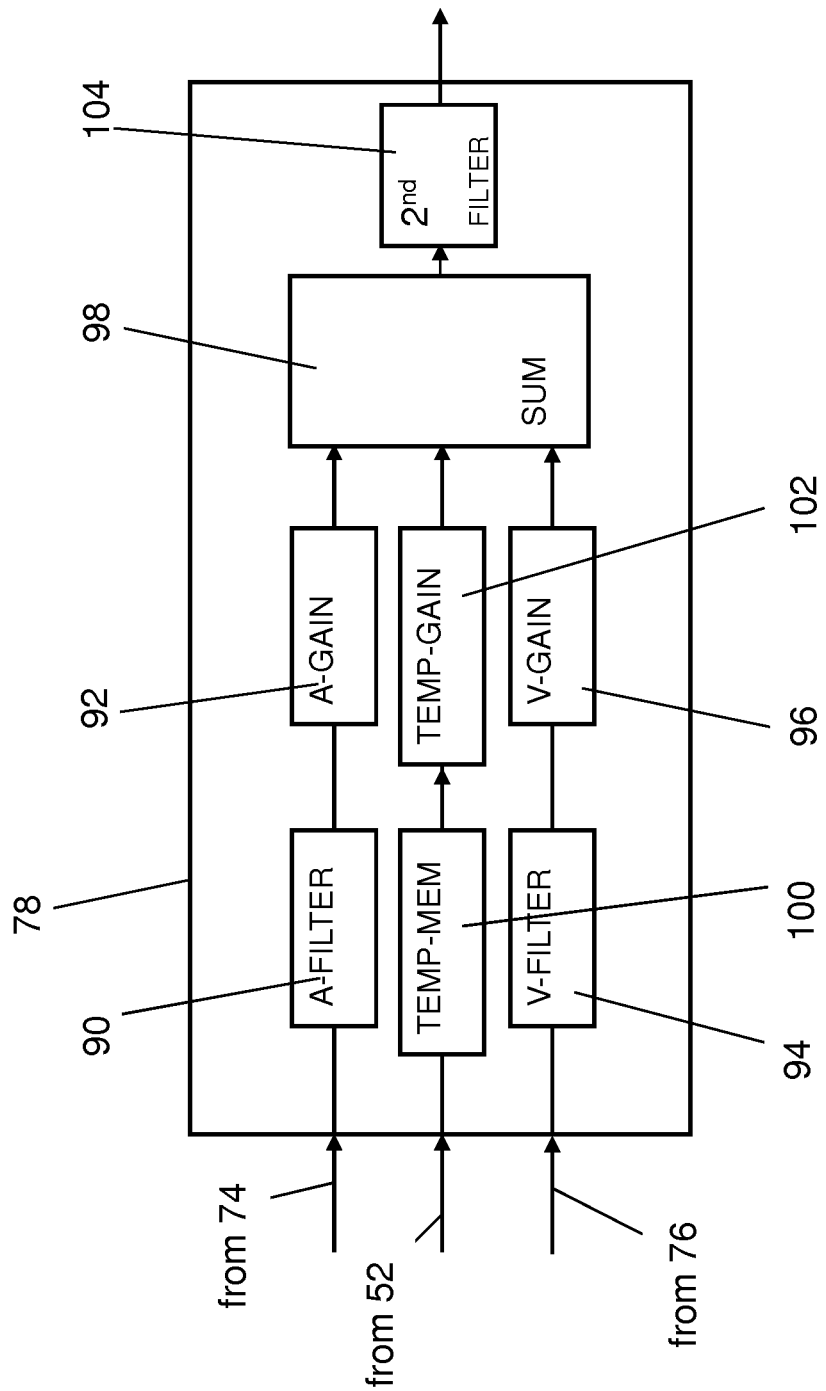
FIG. 3 is a schematic block diagram of an exemplary processing unit for generating a pseudo ECG.

As can be seen in FIG. 3, processing unit 78 includes at least an atrial far-field electrogram filter 90 and an atrial far-field electrogram amplifier 92 that at least indirectly is connected to the atrial far-field electrogram filter 90. The atrial far-field electrogram filter 90 receives signals from the far-field atrial sensing stage 74.

Similarly, a ventricular far-field electrogram filter 94 is provided, receiving an output signal from far-field ventricular sensing stage 76. Far-field electrogram amplifier 92 is connected to the ventricular far-field electrogram filter 94 and is adapted to scale the filtered far-field electrogram signal by a gain factor that may be larger or smaller than (or equal to) one.

Both atrial far-field electrogram amplifier 92 and ventricular far-field electrogram amplifier 96 are connected to a summing stage 98. Summing stage 98 is adapted to sum the synchronized output signals of the atrial far-field electrogram amplifier 92 and the ventricular far-field electrogram amplifier 96 to generate a composite far-field electrogram signal. This composite far-field electrogram signal may be directly fed to a memory 80 or telemetry unit 82 or to control unit 52.

Since the far-field atrial sensing stage 74 and the far-field ventricular sensing stage 76 preferably are blanked during delivery of an atrial and/or ventricular stimulation pulse, no far-field atrial electrogram signal or far-field ventricular electrogram signal can be picked up during blanking of the respective far-field sensing stage 74 or 76. In order to have the composite pseudo far-field electrogram signal (pseudo ECG) more closely resemble a true surface electrogram signal, typical signals appearing in a true surface electrogram signal during atrial or ventricular stimulation are added to the composite far-field electrogram signal. For this purpose, a template memory 100 is provided including templates for the case of atrial stimulation and for the case of ventricular stimulation. The template memory 100 is connected to a template amplifier 102 that can scale the template stored in template memory 100 as necessary. Addition of a template to the composite far-field electrogram signal is triggered by receiving either an atrial marker signal or a ventricular marker signal from control unit 52. Control unit 52 generates an atrial marker signal whenever an atrial stimulation pulse is triggered Likewise, control unit 52 generates a ventricular marker signal whenever a ventricular stimulation pulse is triggered.

For further processing of the pseudo composite far-field electrogram signal, second level filters 104 are provided that are connected to the output off summing stage 98. The second level filters 98 include optimized filters for AS, VS, AP, and VP events, in a window immediately following the respective event types, and a generic filter for the IEGM segment after the window.

A primary objective of the illustrated exemplary apparatus is to determine optimal AVD based on inter-atrial conduction time (IACT), AV nodal recovery time, and autonomic status of the patient.

The following describes an exemplary apparatus and method to determine the optimal AVD after each atrial event by taking into account the inter-atrial conduction time (IACT) (or P-wave duration (PWD)) after an atrial event, an AV nodal recovery time (RT) for the current cycle, and a corresponding autonomic status of the patient. Although the following descriptions do not necessarily differentiate between sensed and paced atrial events, it should be understood that the optimal AVD after a sensed atrial event is generally different than the optimal AVD after a paced atrial event, and they are preferably calculated independently.

According to this exemplary version of the invention, control unit 52 calculates the optimal AVD as PWD plus $\Delta$ duration, where $\Delta$ is a function of the AV nodal recovery time and the underlying autonomic status of the heart. Because the PWD, the AV nodal recovery time, and the autonomic status of the heart can be measured continuously, the beat-to-beat optimal AVD can be calculated in real time.

According to a preferred version, the optimal AVD (AVopt) is determined by:

$$AVopt = PWD + \Delta(RT, AN) \quad (1)$$

where PWD is the measured P wave duration, RT is the recovery time of AV node, AN is an index that measures the autonomic status of the patient, and $\Delta$ is a function of RT and AN.

According to a preferred version, the PWD is measured from the pseudo-ECG that is synthesized from the far-field IEGMs.

One typical sensing configuration is shown in FIGS. 1 and 2, where a bipolar right atrial electrode lead 18 is used for sensing the right atrial far-field electrogram, and a bipolar right ventricular electrode lead 16 is used for sensing the right ventricular far-field electrogram. The sensing of the right atrial far-field electrogram can be programmed in two different unipolar configurations: RA tip 28—Can 12, and RA ring 30—Can 12. Similarly, the sensing of the right ventricular far-field electrogram can be programmed in two different unipolar configurations: RV tip 32—Can 12, and RV ring 34—Can 12. As disclosed previously in U.S. Pat. Appl. No. 2008/0065161, the RA IEGM and the RV IEGM are independently filtered, amplified, and then summed to form the pseudo-ECG.

Four different combinations can be obtained: (1) RA ring—Can combined with RV ring—Can; (2) RA tip—Can combined with RV ring—Can; (3) RA ring—Can combined with RV tip—Can; and (4) RA tip—Can combined with RV tip—Can.

Among these four combinations, the composite signal between RA ring—Can and RV ring—Can (see FIG. 2) is a preferred configuration for PWD measurement. Although not shown, it should be understood that the defibrillation leads can also be used for generating the composite pseudo-ECG. For example, the composite signal between SVC coil—Can and RV coil—Can may also be used for P wave measurement.

Figure 4:
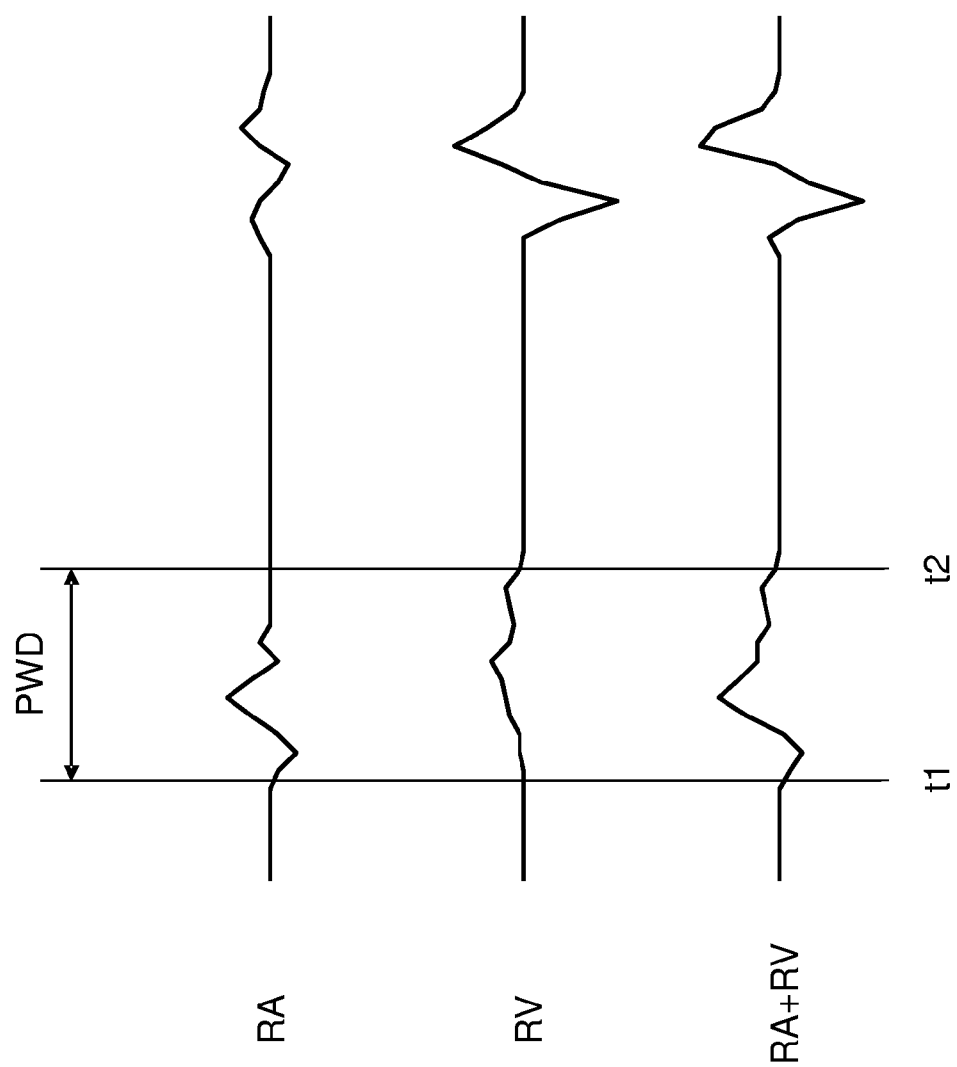
FIG. 4 is a schematic illustration of PWD measurements from pseudo-ECG.

FIG. 4 illustrates the concept of P wave duration measurement from the pseudo-ECG. The top trace shows the right atrial far field intracardial electrogram (RA IEGM), the middle trace shows the right ventricular far field intracardial electrogram (RV IEGM), and the bottom trace shows the composite RA+RV pseudo-ECG. Each trace shows two distinct complexes during each cardiac cycle. The RA IEGM shows an early complex corresponding to the local right atrial depolarization and a late complex corresponding to the far-field ventricular depolarization. The RV IEGM shows an early component corresponding to the far-field left atrial activation and a late component corresponding to the local right ventricular activation. Because of the electrical conduction delay from right atrium to left atrium, the atrial component in RA IEGM appears earlier than that in the RV IEGM. As a result, the atrial component in the composite RA+RV pseudo-ECG is wider than it is measured in either RA IEGM or RV IEGM. For the composite RA+RV pseudo-ECG, the onset of the atrial complex (t1) corresponds to the start of RA activation, and the termination of the atrial complex (t2) corresponds to the end of LA activation. Therefore, the P wave duration (PWD) can be approximated by the duration from t1 to t2.

In the illustrated version, $\Delta$ is inversely related to the recovery time of AV node (RT) when AN is held constant. The RT can be approximated by the R-P interval in the surface ECG or is the V-A interval in the IEGM. According to a preferred version, after each atrial event (paced or sensed), the elapsed duration from the previous ventricular event (paced or sensed) to the present atrial event is considered as the RT of the AV node for the current cardiac cycle.

In the illustrated version, the sympathovagal balance of the patient is continuously monitored by various means, including but not limited to accelerometer sensors, minute ventilation sensors, close-loop-stimulation (CLS) sensors, short-term heart rate variability (HRV) analysis, intracardiac impedance measurements, etc. Preferably, $\Delta$ is increased when the vagal tone is increased or decreased when the sympathetic tone is increased. For example, accelerometer sensors or minute ventilation sensors can be used to detect enhanced sympathetic tone due to physical exertion. In another example, the HRV can be measured using either time or frequency domain methods as known in the art. The low frequency (LF, 0.04-0.15 Hz) band of the HRV is influenced by both the sympathetic and vagal components of the autonomic nervous system, while the high frequency (HF, 0.15-0.40 Hz) band of the HRV is mainly mediated by the vagal outflow. Therefore, a decrease in the LF/HF ratio indicates an increased predominance of the vagal tone, and vice versa. In another version, direct recording of the electrical activity from the vagus nerve can be used to measure the vagal tone. Yet in another version, the autonomic status of the heart can be assessed by measuring the contractility or ventricular filling of the heart based on intracardiac impedance measurement. Furthermore, the inotropic state of the heart can also be measured by pulse pressure, stroke volume, heart sound, chamber volume, etc. Therefore one or more sensors that monitor these physical changes can also be used to independently measure the autonomic status of the heart.

The $\Delta$ function can be defined in different means. One exemplary definition is:

$$\Delta = (\mu + \alpha \cdot e^{-RT/\tau}) \cdot f(r) \quad (2)$$

where $\mu$, $\alpha$, and $\tau$ are all predefined constants, RT is the measured recovery time (V-A interval) of the present beat, and $$f(r) = \frac{K + r^{-1}}{K + 1} \quad (3)$$

where K is a positive constant, and r is the LF/HF ratio defined from the HRV power spectrum. Clearly, when the autonomic status is stable, i.e., no change in r or f(r), $\Delta$ will increase when RT decreases, or decrease when RT increases, and is bounded by $\mu$ and $\mu+\alpha$. Moreover, when RT is held constant, $\Delta$ will increase at enhanced vagal tone due to decrease in r and increase in f(r), whereas $\Delta$ will decrease at enhanced sympathetic tone due to increase in r and decrease in f(r). Obviously, there are many other means to define the $\Delta$ function, and these variations are all within the scope of this invention.

In another version, $\Delta$ may be modulated by intracardiac impedance measurements relating to the ventricular filling or contractility of the heart, which would be necessary if HRV is not measurable during A-V sequential pacing. Alternatively, ventricular filling or contractility may be used to determine $\mu$, $\alpha$, and $\tau$. One problem with other solutions to determine AVD, as stated above, is that $\Delta$ is based on population statistics, which may deviate significantly from any single individual. An automatic and real-time method of determining these constants based on AN is desirable. The optimal filling of the ventricle may be determined by measuring the impedance between, for example, the RV-ring and the RA-ring, thus the fluid in the ventricle is a main determinate of impedance.

Measuring the filling for known states of AN allows μ, α, and τ to be determined for that individual.

For CRT or CRT-D devices, the optimal AVD is further bounded by the intrinsic AV conduction time to avoid ventricular fusion pacing, that is:

$$AVopt = \min(AVI-\delta, PWD + F(RT,AN)) \quad (4)$$

where AVI is the measured intrinsic AV interval, δ is a predefined value, preferably in the range between 10 ms and 40 ms. In other words, the PWD and the intrinsic AV conduction time (AVI) respectively provide the lower boundary and upper boundary of the AVopt, ensuring the calculated optimal AVD is in the physiologically reasonable range. Note that AVI can also be a function of RT and AN, and can be predetermined by a calibration period. For example, the effect of autonomic tone on AVI can be determined by asking the patient to perform a light exercise (change AN) and then measure the corresponding intrinsic AV conduction time at various heart rates. The effect of RT on AVI can be determined by pacing the atrium with different coupling intervals and then measuring the corresponding intrinsic AV conduction time. Preferably, verification of ventricular capture, e.g. by analyzing the morphology of an evoked response, is performed after each ventricular pace at the end of AVD. If ventricular capture is not confirmed, then dynamic increase of δ or reassessment of AVI is performed to ensure that the subsequently-calculated optimal AVD is shorter than the intrinsic AV conduction time.

It will be apparent to those skilled in the art that numerous modifications and variations of the described examples and versions are possible in light of the above teaching. The disclosed examples and versions are presented for purposes of illustration only. Other alternate versions may include some or all of the features disclosed herein. Therefore, it is the intent to cover all such modifications and alternate versions as may come within the true scope of this invention.

What is claimed is:

1. An implantable heart stimulator that can be connected or is connected to at least one electrode lead for picking up electric potentials corresponding to myocardial contraction,
   a. the implantable heart stimulator including:
      i. an evaluation unit that is:
         (1) adapted to being connected to an electrode lead; and
         (2) configured to evaluate electric signals corresponding to electric potentials picked up by the electrode lead; and
      ii. a control unit configured to schedule ventricular stimulation pulses;
   b. wherein:
      i. the evaluation unit is configured to:
         (1) detect an atrial event in a heart from the electric signals corresponding to the electric potentials; and
         (2) determine a P-wave duration of the atrial event from the electric signals corresponding to the electric potentials; and
      ii. the control unit is configured to:
         (1) determine an atrio-ventricular delay on a beat-to-beat basis such that an atrio-ventricular delay for an individual heart cycle depends on the P-wave duration of a same or an immediately preceding heart cycle, wherein:
            (a) the atrio-ventricular delay is calculated as P-wave duration plus Δ duration; and
            (b) Δ is a function of an AV nodal recovery time, the AV nodal recovery time being an interval between an end of a previous AV nodal refractory period and a following AV nodal activation time; and
         (2) schedule a ventricular stimulation pulse to be delivered at the end of the atrio-ventricular delay.

2. The implantable heart stimulator of claim 1, wherein Δ is further a function of an underlying autonomic status of the patient.

3. The implantable heart stimulator of claim 2, wherein Δ is inversely related to the AV nodal recovery time.

4. The implantable heart stimulator of claim 2, wherein the control unit is configured:
   a. to calculate the atrio-ventricular delay on a beat-by-beat basis; and
   b. to adjust Δ on a beat-by-beat basis.

5. The implantable heart stimulator of claim 2, wherein:
   a. Δ is calculated to decrease at increased sympathetic tone; and
   b. Δ is calculated to increase at increased vagal tone.

6. The implantable heart stimulator of claim 2, wherein:
   a. the implantable heart stimulator is configured to determine a V-A interval from an intracardiac electrocardiogram derived from picked up electric potentials; and
   b. the control unit is configured to approximate the AV nodal recovery time based on the V-A interval.

7. The implantable heart stimulator of claim 2, wherein:
   a. the implantable heart stimulator includes at least one of an accelerometer sensor, a minute ventilation sensor, and a close-loop-stimulation sensor; and
   b. the control unit is configured to assess the autonomic status of the heart via the accelerometer sensor, the minute ventilation sensor, the close-loop-stimulation sensor, a short-term heart rate variability analysis, and/or intracardiac impedance measurements.

8. The implantable heart stimulator of claim 2, wherein:
   a. the heart stimulator is configured to deliver a cardiac resynchronization therapy; and
   b. the control unit is further configured to bound the atrio-ventricular delay by an intrinsic atrioventricular conduction time.

9. A method to determine an atrio-ventricular delay on a beat-to-beat basis, the method including the steps of:
   a. determining a P-wave duration from electric signals corresponding to electric potentials in a heart; and
   b. determining the atrio-ventricular delay on a beat-to-beat basis such that the atrio-ventricular delay for an individual heart cycle depends on the P-wave duration of a same or an immediately preceding heart cycle, wherein:
      i. the atrio-ventricular delay is calculated as P-wave duration plus Δ duration; and
      ii. Δ is a function of an AV nodal recovery time, the AV nodal recovery time being an interval between an end of a previous AV nodal refractory period and a following AV nodal activation time.

10. The method of claim 9, wherein Δ is further a function of an underlying autonomic status of the patient.

11. The method of claim 10, wherein Δ is inversely related to the AV nodal recovery time.

12. The method of claim 10, wherein the atrio-ventricular delay is calculated on a beat-by-beat basis and Δ is adjusted on a beat-by-beat basis.

13. The method of claim 10 further including the steps of:
   a. determining a V-A interval from an intracardiac electrocardiogram derived from picked up electric potentials; and
   b. approximating the AV nodal recovery time using the V-A interval.

14. The method of claim 10, wherein the autonomic status of the heart is assessed via an accelerometer sensor, a minute ventilation sensor, close-loop-stimulation (CLS) sensors, short-term heart rate variability (HRV) analysis, and/or intracardiac impedance measurements.

15. The method of claim 10, wherein the atrioventricular delay is further bound by an intrinsic atrioventricular conduction time.

16. The method of claim 10, wherein $\Delta$ decreases at increased sympathetic tone and $\Delta$ increases at increased vagal tone.

17. An implantable heart stimulator configured to determine atrio-ventricular delay on a beat-to-beat basis by:
   a. determining a P-wave duration from electric signals corresponding to electric potentials in a heart; and
   b. determining an atrio-ventricular delay on a beat-to-beat basis such that the atrio-ventricular delay for an individual heart cycle depends on the P-wave duration of a same or an immediately preceding heart cycle, wherein:
      i. the atrio-ventricular delay is calculated as P-wave duration plus $\Delta$ duration; and
      ii. $\Delta$ is a function of an AV nodal recovery time, the AV nodal recovery time being an interval between an end of a previous AV nodal refractory period and a following AV nodal activation time.

18. The implantable heart stimulator of claim 17 including:
   a. an electrode lead configured to pick up electric potentials corresponding to myocardial contraction;
   b. an evaluation unit connected to the electrode lead, the evaluation unit being configured to evaluate electric signals corresponding to the electric potentials; and
   c. a control unit configured to schedule a ventricular stimulation pulse to be delivered at the end of the atrio-ventricular delay following an atrial event.

19. The implantable heart stimulator of claim 18 wherein the control unit is further configured to calculate:
   a. the atrioventricular delay where $\Delta$ is further a function of an underlying autonomic status of the patient; and
   b. the atrioventricular delay on a beat-by-beat basis and to adjust $\Delta$ on a beat-by-beat basis.

20. The implantable heart stimulator of claim 19, wherein:
   a. the implantable heart stimulator is configured to determine a V-A interval from an intracardiac electrocardiogram derived from picked up electric potentials; and
   b. the control unit is further configured to approximate the AV nodal recovery time based on the V-A interval.

21. The implantable heart stimulator of claim 1, wherein $\Delta$ is substantially defined by $\Delta = (\mu + \alpha \cdot e^{-RT/\tau}) \cdot f(r)$, where:
   a. $\mu$, $\alpha$, and $\tau$ are predefined constants;
   b. RT is the AV nodal recovery time of the present beat;
   c.
   $$f(r) = \frac{K + r^{-1}}{K + 1};$$
   d. K is a positive constant; and
   e. r is a ratio of low frequency to high frequency from a heart rate variability analysis.

22. The method of claim 9, wherein $\Delta$ is substantially defined by $\Delta = (\mu + \alpha \cdot e^{-RT/\tau}) \cdot f(r)$, where:
   a. $\mu$, $\alpha$, and $\tau$ are predefined constants;
   b. RT is the AV nodal recovery time of a present beat;
   c.
   $$f(r) = \frac{K + r^{-1}}{K + 1};$$
   d. K is a positive constant; and
   e. r is a ratio of low frequency to high frequency from a heart rate variability analysis.

23. The implantable heart stimulator of claim 17, wherein $\Delta$ is substantially defined by $\Delta = (\mu + \alpha \cdot e^{-RT/\tau}) \cdot f(r)$, where:
   a. $\mu$, $\alpha$, and $\tau$ are predefined constants;
   b. RT is the AV nodal recovery time of a present beat;
   c.
   $$f(r) = \frac{K + r^{-1}}{K + 1};$$
   d. K is a positive constant; and
   e. r is a ratio of low frequency to high frequency from a heart rate variability analysis.

* * * * *